United States Patent [19]

Pozzo

[11] Patent Number: 5,092,847
[45] Date of Patent: Mar. 3, 1992

[54] ENTERAL FEEDING TUBE STYLET

[75] Inventor: Dennis M. Pozzo, Florissant, Mo.

[73] Assignee: Sherwood Medical Company, St. Louis, Mo.

[21] Appl. No.: 505,876

[22] Filed: Apr. 6, 1990

[51] Int. Cl.$^5$ .............................................. A61M 25/00
[52] U.S. Cl. .................................. 604/170; 604/164; 128/658; 128/772
[58] Field of Search ............... 604/43, 93, 164, 165, 604/170, 270, 280–283; 128/657, 772

[56] References Cited

U.S. PATENT DOCUMENTS

| Re. 32,306 | 12/1986 | Waters | 604/165 |
|---|---|---|---|
| 3,773,034 | 11/1973 | Burns et al. | 128/657 |
| 3,973,556 | 8/1976 | Fleischhacker et al. | 128/2 M |
| 4,033,331 | 7/1977 | Guss et al. | 128/2 M |
| 4,270,542 | 6/1981 | Plumley | 128/350 R |
| 4,349,024 | 9/1982 | Ralston, Jr. | 128/247 |
| 4,461,280 | 7/1984 | Baumgartner | 604/170 |
| 4,534,363 | 8/1985 | Gold | 128/772 |
| 4,601,713 | 7/1986 | Fuqua | 604/170 |
| 4,636,200 | 1/1987 | Vaillancourt | 604/170 |
| 4,659,328 | 4/1987 | Potter et al. | 604/170 |
| 4,661,110 | 4/1987 | Fortier et al. | 604/256 |
| 4,668,225 | 5/1987 | Russo et al. | 604/270 |
| 4,676,249 | 6/1987 | Arenas et al. | 128/657 |
| 4,705,709 | 11/1987 | Vailancourt | 428/36 |
| 4,854,330 | 8/1989 | Evans, III et al. | 128/772 |
| 4,874,365 | 10/1989 | Frederick et al. | 604/54 |
| 4,895,168 | 1/1990 | Machek | 604/170 |
| 4,928,669 | 5/1990 | Sullivan | 128/772 |
| 4,930,521 | 6/1990 | Metzger et al. | 128/786 |
| 4,934,380 | 6/1990 | de Toledo | 128/772 |

FOREIGN PATENT DOCUMENTS 1185862  10/1982  Canada .
2380034  2/1977  France .

Primary Examiner—C. Fred Rosenbaum
Assistant Examiner—Chalin Smith
Attorney, Agent, or Firm—Allison: Richard D.; Montgomery W. Smith; Curtis D. Kinghorn

[57] ABSTRACT

A stylet for use with a flexible feeding tube including a proximal stylet hub connected to the proximal end of a stylet wire and an elongate and flexible sleeve and cylindrically-shaped urethane member attached to the distal end of the stylet wire such that the sleeve member and stylet wire are adapted not to inadvertently pierce the feeding tube and the sleeve member is sufficiently flexible so that it will not cause excessive trauma to the tissues of the patient during intubation of the feeding tube if the sleeve member is inadvertently manipulated to extend through the side holes of the feeding tube.

8 Claims, 2 Drawing Sheets

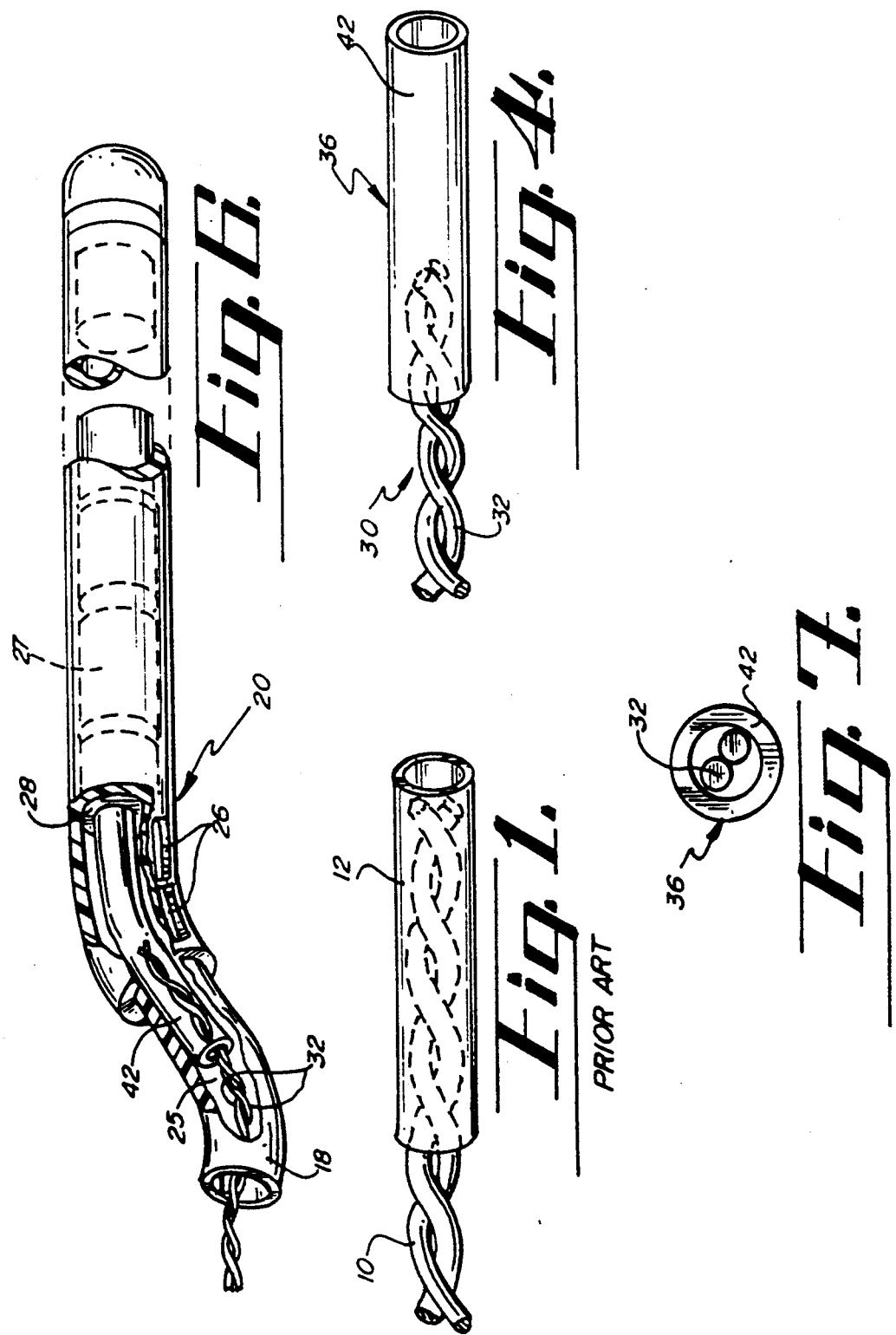

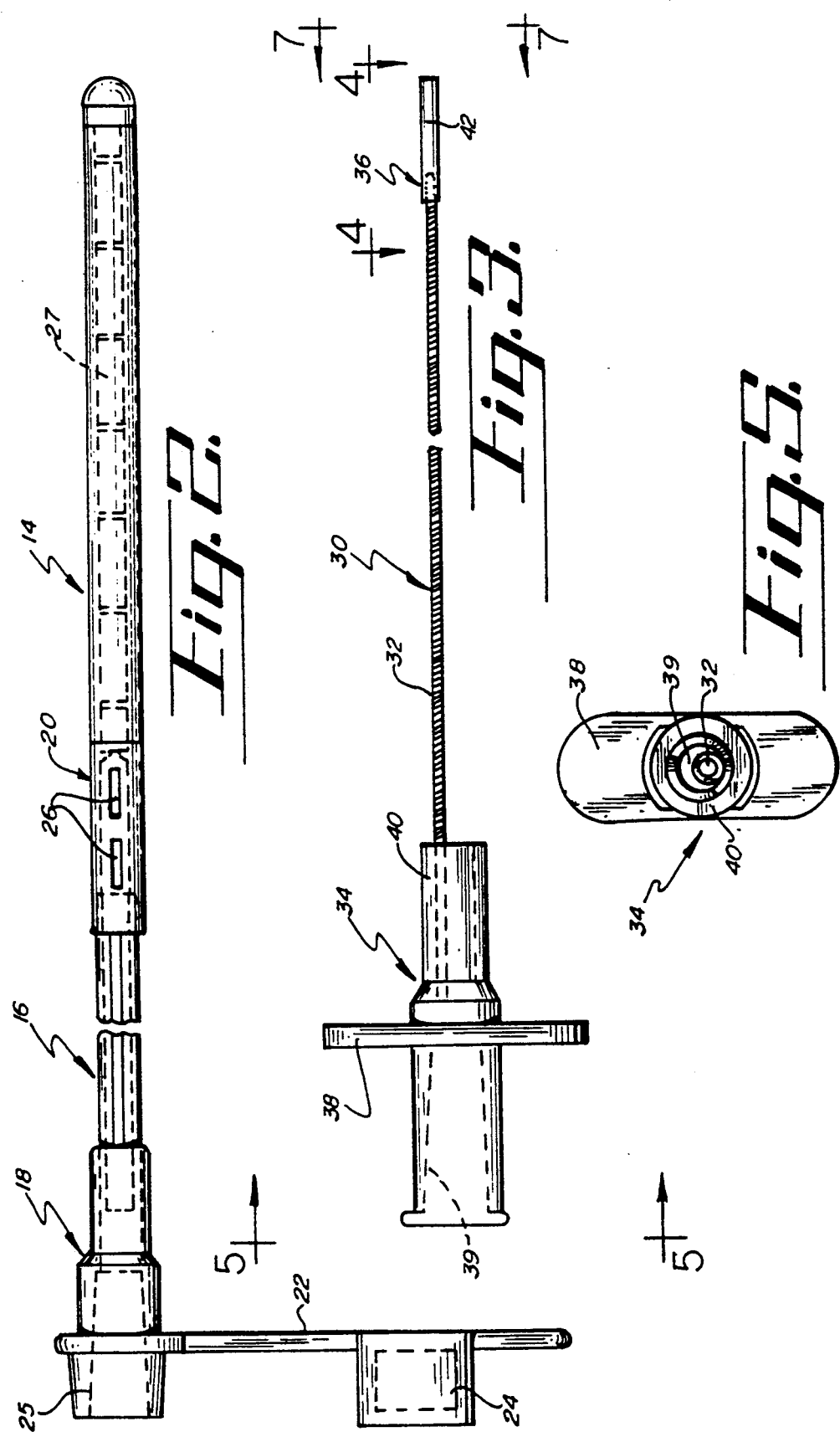

ENTERAL FEEDING TUBE STYLET

FIELD OF THE INVENTION

The present invention relates generally to enteral feeding tubes and more particularly to an improved stylet for use during the insertion of an enteral feeding tube into the stomach or duodenum of a patient.

BACKGROUND OF THE INVENTION

Enteral feeding tubes in one form or another have been used for a number of years to supply nutritional fluids to a patient. Typically, such devices consist of four parts or elements, namely, a flexible feeding tube for delivering nourishment to the patient, a semi-rigid stylet for positioning the feeding tube in the stomach or duodenum of the patient, a bolus tube section and weight for retaining the feeding tube in the stomach or duodenum of the patient and a connector on the proximal end of the feeding tube for attachment of the supply of nutritional fluid to the feeding tube.

A principal problem associated with feeding tubes is their proper placement within the patient. The feeding tube is preferably constructed of a soft and extremely flexible material so as to cause as little pain and trauma to the patient as possible during insertion of the feeding tube and to increase the length of time a patient may be intubated. To enable the insertion of a flexible feeding tube through the nose and down into the stomach or duodenum of a patient, the rigidity of the tube must be increased during he intubation procedure. One commonly used approach to increase the rigidity of the feeding tube during intubation is by removably mounting a semi-rigid stylet in the feeding tube. This approach allows the user to use a flexible feeding tube to provide nutritional fluid to a patient while increasing the rigidity of the feeding tube during the insertion of the feeding tube into the patient. Once the feeding tube has been properly positioned in the patient, the stylet is removed from the feeding tube so that the feeding tube will be flexible during the time it is within the patient.

Early stylets consisted of an elongate wire having a solid plug member on the proximal end thereof to allow the stylet to be removably retained in the connector on the proximal end of the feeding tube and an enlarged ball-shaped stylet tip formed on the distal end of the stylet wire. The early stylets were generally disfavored because the stylet tip would occasionally pierce the feeding tube and traumatize the patient tissues as the feeding tube was being inserted into the patient. On other occasions, the stylet tip would pass through the side holes of the feeding tube and traumatize the patient tissues as the feeding tube was being inserted into the patient.

One approach to solving this problem has been to increase the diameter of the stylet tip so that it is less likely to pierce the feeding tube and will not pass through the side holes of the feeding tube. One example of this approach is U.S. Pat. No. 4,659,328 granted to Potter et al which discloses the use of a helically coiled small diameter wire on the distal end of the stylet wire. As described in the Potter et al patent, the coils of the wire are oriented transversely to the longitudinal axis of the stylet wire and are dimensioned such that the stylet tip is prevented from exiting the feeding tube by passing through the side holes in the feeding tube. This patent also discloses that the length of the stylet wire is chosen so that the stylet tip is compressed against the end wall of the feeding tube when the stylet is inserted into the feeding tube. A similar stylet having a small diameter wire stylet tip is disclosed in U.S. Pat. No. 4,636,200 granted to Vaillancourt which is assigned to Sherwood Medical Company and incorporated herein by reference as if fully set forth herein. U.S. Pat. No. 4,496,347 granted to MacLean et al also discloses an enlarged wire stylet tip which is described as being sized such that the stylet tip is prevented from piercing the feeding tube or passing through a side hole in the feeding tube. The stylet of Maclean et al consists of a single or stranded wire which is bent in half and then twisted about itself to form a double helix and so that the stylet tip is an elongated wire loop of a variable size.

Yet another approach is illustrated in FIG. 1 where the stylet is formed of a twisted wire and includes a PVC sleeve bonded to the distal end of the stylet wire. As illustrated, the sleeve extends only slightly beyond the distal end of the stylet wire and functions primarily to prevent the stylet wire from fraying and possibly piercing the feeding tube. The stylet wire and sleeve are sized such that the distal end of the sleeve extends to a location proximally of the side holes of the bolus tube when the stylet hub is placed in the connector on the proximal end of the feeding tube.

The preferred stylet is simple and economical to manufacture and will not cause excessive trauma to the patient if the stylet tip should inadvertently pierce the feeding tube or extend through the side holes of the feeding tube. The stylet tips disclosed by Potter et al and Vaillancourt, as described above, are relatively complex to manufacture and the use of a wire stylet tip may cause excessive trauma to the patient if the stylet tip pierces the feeding tube or is deflected to extend through the side holes of the feeding tube. The stylet tip disclosed by MacLean et al, as described above, is relatively simple to manufacture but is easily deformed and may cause excess trauma to the patient if the stylet tip pierces the feeding tube or is deflected to extend through the side holes of the feeding tube. The approach illustrated in FIG. 1 is simple to manufacture but forms a relatively rigid stylet tip which will not adequately protect the tissues of the patient from trauma. The rigidity of this prior art stylet tip is due to the presence of the stylet wire within substantially the entire length of the sleeve and therefore, the stylet tip of this device may cause excessive trauma to the tissues of the patient if the relatively rigid stylet tip inadvertently pierces the feeding tube. Additionally, by terminating the stylet tip near the proximal end of the bolus tube section, there is an increased likelihood that the feeding tube will bend or possibly even separate at the junction of the feeding tube and the bolus tube section.

Although the above described stylets purportedly will not pierce the feeding tube or pass through the side holes of the feeding tube, many hospitals still require that physicians intubate their own patients due to the likelihood that the wire stylet tip may pierce the feeding tube or extend through the side holes of the feeding tube if the feeding tube and stylet are improperly inserted into the patient. The use of a wire or rigid stylet tip in the present devices will significantly increase the severity of the injury to the patient if the feeding tube is improperly inserted into the patient.

Therefore, a need remains for a stylet which is simple and inexpensive to manufacture and will not pierce the feeding tube and which will not cause excessive trauma to the tissues of the patient if it is inadvertently manipulated to extend through the side holes of the feeding tube.

SUMMARY OF THE INVENTION

The stylet of the present invention solves the above described problems by providing a simple and inexpensively manufactured stylet which will not pierce the feeding tube and which will not cause excessive trauma to the tissues of the patient if it is somehow manipulated to extend through the side holes of the feeding tube.

The stylet of the present invention preferably consists of a hollow proximal connector or hub, an elongate and twisted small diameter wire and a stylet tip formed of an elongate and flexible urethane sleeve member, the majority of which extends beyond the distal end of the stylet wire. The length of the stylet wire is chosen so that when the stylet hub is inserted into the connector on the proximal end of the feeding tube, the stylet wire will extend to a location generally proximal to the side holes and adjacent to the proximal end of the bolus tube. The sleeve member is mounted on the distal end of the stylet wire and is sized to extend beyond the distal end of the stylet wire so that the sleeve will be compressively held in position within the bolus tube section of the feeding tube by frictional contact with the end wall formed at the distal end of the bore in the feeding tube when the stylet hub is inserted into the connector on the proximal end of the feeding tube. The maximum exterior diameter of the stylet wire and sleeve member are chosen so that the flow of fluids through the bore of the feeding tube are not substantially impaired by the presence of the stylet wire and sleeve member within the relatively small diameter feeding tube. The stylet of the present invention is readily adaptable for use with nearly all of the presently available feeding tubes, including those which have multiple ports or Y-connectors such as the feeding tube illustrated in U.S. Pat. No. 4,874,365 granted to Frederick et al which is incorporated herein by reference.

The present invention is readily useable with intubation procedures where the position of the feeding tube is confirmed by the injection of air or liquid through the proximal connector into the patient. Alternately, the present invention may be used with feeding tubes where the position of the feeding tube is confirmed by withdrawing fluids from the patient through the feeding tube or where X-rays are used to confirm the position of the feeding tube within the stomach or duodenum of the patient.

BRIEF DESCRIPTION OF THE DRAWINGS

FIG. 1 is an enlarged sectional view showing a prior art stylet tip as described herein;

FIG. 2 is an elevated side view, partially cutaway, showing a feeding tube of the type used with the present invention;

FIG. 3 is an elevated side view, partially cutaway, showing the stylet of the present invention;

FIG. 4 is an enlarged sectional view taken along line 4—4 of FIG. 3 showing the stylet wire and stylet tip of the present invention;

FIG. 5 is an enlarged end view taken along line 5—5 of FIG. 3 showing the stylet hub of the present invention;

FIG. 6 is an enlarged sectional view of the stylet wire and stylet tip as shown in FIG. 4 inserted in the distal end of a partially cutaway feeding tube as shown in FIG. 2; and FIG. 7 is a partial end view of the present invention taken along lines 7—7 of FIG. 3 showing the distal end of the stylet wire and stylet tip.

DETAILED DESCRIPTION OF THE PREFERRED EMBODIMENT

Referring to FIG. 1, there is shown a prior art stylet of known construction. As shown in FIG. 1, the prior stylet consists of a twisted small diameter stylet wire 10 and a sleeve member 12 consisting of a polyvinylchloride plastic. The sleeve member 12 is adhesively bonded to the stylet wire 10 such that the distal end of the stylet wire 10 is enclosed by nearly the entire length of the sleeve member 12 to prevent the strands of the stylet wire 10 from fraying. The stylet wire 10 and sleeve member 12 of this device are sized such that when the stylet is inserted into the feeding tube, the distal end of the sleeve member 12 will terminate proximally of the side holes of the feeding tube.

As described more fully hereinafter, the stylet 30 of the present invention is particularly adapted for use in a feeding tube 14 of the type illustrated in FIG. 2. The feeding tube 14 shown in FIG. 2 is an enteral feeding tube available from Sherwood Medical Company of St. Louis, Mo., USA which is described as being an 8 or 12 French tube and which may be either 110 cm or 92 cm long. The feeding tube 14 as shown in FIGS. 2 and 6 is an 8 French feeding tube and consists of an elongate polyurethane flexible feeding tube section 16, a hollow connector member 18 having a distal end which is adapted to be connected to the proximal end of the tube section 16 and a semi-rigid bolus tube 20 adapted to be connected to the distal end of the tube section 16.

As shown in FIG. 2, the proximal end of the connector member 18 is adapted to receive the stylet hub 34 of the present invention as described hereinafter, or a source of liquid nourishment therein (not shown). As illustrated, the connector member also includes a flexible strap member 22 and hub 24 attached thereto to allow the user to close the proximal end of the connector member 18 when the feeding tube 14 is not in use by placing the hub 24 over the proximal end of the connector member 18.

The bolus tube section 20 of the feeding tube 14 is constructed of a semi-rigid plastic or of a thicker polyurethane than the feeding tube 14 such that the bolus tube section 20 is more rigid than the tube section 16 and has an outer diameter slightly larger than the outer diameter of the tube section 16. A relatively small diameter inner bore 25 extends from the connector member 18 and the tube section 16 into the proximal end thereof. The bolus tube section 20 of the 8 French feeding tube 14 includes a pair of oppositely facing and preferably rectangularly-shaped side holes 26 near the proximal end of the bolus tube section 20 in flow communication with the bore 25 to allow nutritional fluids to be delivered therethrough. The bolus tube section 20 also includes a weighted distal end having a plurality of elongate and cylindrical weights 27 enclosed therein. An end wall 28 is located slightly distal to the distal side of the side holes 26 at the distal end of the bore 25 in the interior of the bolus tube section 20, the function of which is described more fully hereinafter.

As illustrated in FIG. 3, the stylet 30 of the present invention generally includes an elongate and braided or twisted stylet wire 32, a proximal stylet hub 34 attached to the proximal end thereof and a flexible stylet tip 36 attached to the distal end of the stylet wire 32. The stylet wire 32 is preferably constructed of a small diameter wire which is braided or twisted such that the maximum outer diameter is preferably less than 0.9 mm. The proximal end of the stylet wire 32 is preferably adhesively bonded to the distal end of the stylet hub 34. The stylet hub 34 includes an enlarged and generally oval-shaped finger member 38 positioned approximately midway along the body section 40 of the stylet hub 34. The outer diameter of the body section 40 which is located distally of the finger member 38 is sized to frictionally fit within proximal end of the connector member 18 on the proximal end of the feeding tube 14. The inner diameter of the body section 40 which is located proximal of the finger member 38 is sized to receive the luer tip of a syringe (not shown) or other device therein. The flow-through style of stylet hub 34 as shown in FIGS. 3 and 5 includes a hollow passageway 39 extending therethrough to allow fluid to flow therethrough while the stylet 30 is positioned in the feeding tube 14 to enable the user to verify the position of the feeding tube 14 in the patient without removing the stylet hub 34 from the connector member 18.

The stylet tip 36 of the present invention consists of an elongate and cylindrical sleeve member 42 which is constructed of a flexible plastic such as urethane. The sleeve member 42 is preferably adhesively bonded to the distal end of the stylet wire 32 such that the majority of the sleeve member 42 extends beyond the stylet wire 32. The external diameter of the sleeve member 42 is slightly smaller than the inner diameter of the bore 25 of the feeding tube 14 to allow fluid to flow past the sleeve member when the stylet 30 is positioned in the feeding tube 14. In the preferred embodiment, the external diameter of the sleeve member 42 preferably is between 1 and 2 mm and more preferably 1.25 mm. The internal diameter of the sleeve member 42 is slightly larger than the maximum external diameter of the twisted stylet wire 32.

In the preferred embodiment, the internal diameter of the sleeve member 42 is between 0.6 and 0.9 mm and more preferably 0.8 mm such that the preferred wall thickness of the sleeve member 42 is between 0.1 and 0.2 mm. The use of a cylindrical sleeve member 42 having a reduced wall thickness for the stylet tip 36 of the present invention provides a stylet tip 36 which may be compressed against the end wall 28 of the bolus tube section 20 to increase the overall rigidity of the stylet 30 in the feeding tube 14 while still having sufficient flexibility so that the stylet tip 36 will not injure the patient if it is inadvertently extended through the side holes 26 of the feeding tube 14. In the preferred embodiment, the sleeve member has a greater flexibility than the stylet wire 32 and bolus tube section 20 and generally the same flexibility as the feeding tube 14.

The stylet tip 36 of the present invention is preferably between 20 and 30 mm long and is positioned on the distal end of the stylet wire 32 such that at least half of the sleeve member 42 extends beyond the distal end of the stylet wire 32 or such that between 12.5 and 15.0 mm or more preferably approximately 13.8 mm of a 25 mm long sleeve member 42 extends beyond the distal end of the stylet wire 32. In the preferred form of the present invention, it has been found to be desirable to have between 11.0 and 12.5 mm or more preferably 11.6 mm of the stylet wire 32 extending into the sleeve member 42 so that the stylet tip 36 does not fall off the stylet wire 32 during the insertion of the stylet 30 into the feeding tube 14 or during the insertion of the feeding tube 14 and stylet 30 into the patient.

The length of the stylet wire 32 is chosen so that when the stylet hub 34 of the stylet 30 is inserted in the connector member 18 of the feeding tube 14, the distal end of the stylet wire 32 will terminate adjacent to the proximal end of the bolus tube section 20 and proximally of the side holes 26 so that the stylet wire 32 cannot project through the side holes 26 of the bolus tube section 20. The wall thickness of the sleeve member 42 is such that the distal end of the stylet wire 32 will not readily pierce the sleeve member 42 and therefore, is also prevented from piercing the wall of the feeding tube 14. The length of the stylet wire 32 and the length of the sleeve member 42 extending beyond the stylet wire 32 are particularly selected so that when the stylet 30 is fully inserted into the feeding tube 14, the distal end of the sleeve member 42 will frictionally contact the end wall 28 of the bolus tube section 20 so that the distal end of the sleeve member 42 is positioned distal to the side holes 26 of the bolus tube section 20 and the sleeve member 42 is compressively held against the end wall 28 of the bolus tube section 20. The compression of the sleeve member 42 against the end wall 28 of the bolus tube 20 increases the rigidity of the stylet 30 in the feeding tube 14 so that the outer diameter of the stylet wire 32 may be reduced while still providing the rigidity necessary for the proper insertion of the feeding tube 14 into the patient. Additionally, the compressive contact between the sleeve member 42 and the end wall 28 decreases the likelihood that the feeding tube 14 will bend or separate at the junction of the feeding tube 14 and the proximal end of the bolus tube section 20.

As briefly described above and illustrated in FIGS. 2 and 6, the side holes 26 of the feeding tube 14 are generally rectangularly-shaped and radially spaced apart near the proximal end of the bolus tube section 20 of the 8 French feeding tube. In the 12 French tube (not shown), the bolus tube section includes three radially spaced side holes having a larger perimeter than the side holes 26 of the 8 French feeding tube. As shown in FIG. 2, the side holes 26 preferably have a width between 1.0 and 1.5 mm and more particularly about 1.3 mm and a length between 3 and 5 mm and more particularly about 4 mm such that the perimeter of the side holes 26 is greater than the perimeter of the stylet tip 36. The side holes 26 are sized to allow the maximum fluid flow therethrough without substantially weakening the bolus tube section 20. If the side holes 26 are too small, the side holes 26 will become occluded and the nutritional fluid will not be properly delivered to the patient.

In the past, if the manufacturer desired to increase the size of the side holes 26, the circumference of the stylet tip would be increased accordingly so that the stylet tip would not inadvertently project through the side holes of the feeding tube. Alternately, the length of the stylet 30 would be decreased so that the stylet tip 36 would extend to a location proximally of the side holes 26. The rigidity of the stylet wire 32 would also be increased to compensate for the loss of stylet 30 rigidity caused by not being able to compress the stylet tip 36 against the end wall 28 of the bolus tube section 20. An example of this approach is illustrated in FIG. 1 and described above. If the size of the side holes 26 were increased without reducing the length of the stylet wire 32, the metal or rigid stylet tip 36 of the prior devices could be deflected from their position against the end wall 28 of the bolus tube section 20 to extend through the side holes 26 and would cause unnecessary trauma to the tissues of the patient as the feeding tube 14 is inserted into the stomach or duodenum of the patient. The sleeve member 42 of the present invention allows the size of the side holes 26 to be determined irrespective of the circumference of the stylet tip 36 or the length of the stylet wire 32 because the sleeve member 42 is initially compressed against the end wall 28 of the bolus tube section 20 to increase the rigidity of the stylet and even if the stylet tip 36 is inadvertently manipulated such that it extends through one of the side holes 26, the increased flexibility of the sleeve member 42 will not cause excessive trauma to the tissues of the patient as the feeding tube 14 is inserted into the patient.

What is claimed is:

1. A feeding tube assembly comprising:
    a flexible tube section having proximal and distal ends and a bore extending therethrough, said tube section having a predetermined inner diameter and length for the selective administration and aspiration of fluids from the gastrointestinal tract of a patient,
    a hollow connector member operatively connected to said proximal end of said tube section, said connector member including a bore therein in communication with said bore of said tube section,
    a semi-rigid bolus tube section including a proximal end operatively connected to said distal end of said tube section, a closed distal end extending distally from said proximal end and a bore extending through said proximal end of said bolus tube section in communication with a plurality of side holes and said bore terminating in an end wall located proximal to the distal end of said bolus tube section and wherein said bolus tube section is less flexible than said tube section,
    a stylet hub member, adapted to be removably retained in said connector member,
    an elongate and semi-rigid wire having proximal and distal ends and an outer diameter smaller than the diameter of said bore of said tube section, said proximal end of said wire being operatively connected to said hub member and said wire having a predetermined length such that when said hub member is inserted into said connector member, said distal end of said wire is positioned near said proximal end of said bolus tube section, and
    a flexible and elongate stylet tip member having a first and a second section wherein said tip member has a substantially uniform outer diameter which is less than the inner diameter of said bore of said bolus tube section, said outer diameter of said tip member being preferably between 1 and 2 mm and said outer diameter of said tip member being smaller than the smallest diameter of said side holes in said bolus tube and wherein said first section of said tip member is operatively connected to said distal end of said wire and said second section extends distally from said distal end of said wire to form a hollow and deformable stylet tip extending from the distal end of said wire.

2. The feeding tube assembly of claim 1, wherein said stylet tip is adapted to contact said end wall of said bolus tube to increase the rigidity of said wire when said hub member is inserted into said connector member.

3. The feeding tube assembly of claim 1, wherein said tip member is a cylindrical sleeve member having a wall thickness between 0.1 and 0.2 mm and an internal diameter between 0.6 and 0.9 mm.

4. A feeding tube assembly comprising:
    a flexible tube section having proximal and distal ends and a bore extending therethrough, said tube section having a predetermined inner diameter and length for the administration of fluids into the gastrointestinal tract of a patient,
    a hollow connector member operatively connected to said proximal end of said tube section, said connector member including a bore therein in communication with said bore of said tube section,
    a semi-rigid bolus tube section having proximal and distal ends, said proximal end including a bore therein in flow communication with said bore of said tube section and being operatively connected to said distal end of said tube section, a closed and weighted distal end extending distally of said proximal end and a plurality of spaced apart side holes having a predetermined size and said side holes being located near the proximal end of said bolus tube section in flow communication with said bore of said bolus tube section and bore of said tube section,
    a stylet hub member adapted to be removably received in said connector member,
    an elongate and semi-rigid stylet wire having a proximal end operatively connected to said hub member and an outer diameter smaller than the diameter of said bore of said tube section, said wire having a predetermined length and a distal end such that when said hub member is received in said connector member said distal end of said wire is adjacent the proximal end of said bolus tube section and proximal to said side holes of said bolus tube section,
    a flexible and cylindrically shaped sleeve member having a generally uniform outer diameter and a first and a second longitudinal section, the perimeter of said sleeve member being less than the perimeter of said side holes in said bolus tube section, said first section adapted to enclose a sufficient portion of said distal end of said wire to retain said sleeve member thereon when said stylet hub is inserted into said connector member and said second section being adapted to extend a sufficient distance distally from said distal end of said wire to contact said end wall of said bolus tube section and said second section including an external diameter less than the diameter of said bore of said tube section and an internal diameter between 0.6 and 0.9 mm.

5. A feeding tube assembly comprising:
    a flexible tube section having proximal and distal ends and a bore extending therethrough, said tube section having a predetermined inner diameter and length for the selective administration and aspiration of fluids from the gastrointestinal tract of a patient,
    a hollow connector member operatively connected to said proximal end of said tube section, said connector member including a bore therein in communication with said bore of said tube section,
    a semi-rigid bolus tube section including a proximal end operatively connected to said distal end of said tube section, a closed distal end extending distally from said proximal end and a bore extending through said proximal end of said bolus tube section in communication with a plurality of side holes and said bore terminating in an end wall located proximal to the distal end of said bolus tube section and wherein said bolus tube section is less flexible than said tube section, a stylet hub member, adapted to be removably retained in said connector member, an elongate and semi-rigid wire having proximal and distal ends and outer diameter smaller than the diameter of said bore of said tube section, said proximal end of said wire being operatively connected to said hub member and said wire having a predetermined length such that when said hub member is inserted into said connector member, said distal end of said wire is positioned near said proximal end of said bolus tube section, and a flexible and elongate stylet tip member having a first and a second section wherein said tip member has a substantially uniform outer diameter which is less than the inner diameter of said bore of said bolus tube section, said first section of said tip member being operatively connected to said distal end of said wire and said second section extending distally from said distal end of said wire to form a hollow and deformable stylet tip extending from the distal end of said wire, said second section of said tip member being longer than said first section of said tip member and said second section extending from a position proximally of said side holes in said bore in said bolus tube section to said end wall of said bolus tube section when said hub member is inserted into said connector member and said wire is inserted into said bore of said tube section, the perimeter of said second section of said tip member being less than the perimeter of said side holes on said bolus tube.

6. A stylet for stiffening a flexible feeding tube used for the selective administration or aspiration of fluids from the gastrointestinal tract of a patient wherein the tube includes a proximal end having at least one proximal connector thereon, a weighted distal end, spaced side holes located proximally of the weighted distal end and a bore extending through the tube from the proximal connector to an end wall located in the tube and positioned distally of the side holes on the tube for fluid communication between the proximal connector and the side holes, the stylet comprising:

an elongate stylet wire having proximal and distal ends, said wire being adapted to extend through the bore of the tube such that when said proximal end of said wire is positioned adjacent to the proximal end of the tube, said distal end of said wire is positioned proximally of the side holes on the tube, a proximal stylet hub operatively connected to said proximal end of said wire, said stylet hub being adapted to be frictionally and releasably retained in the proximal end of the tube such that said wire extends therefrom into the bore of the tube, and a flexible and cylindrical plastic sleeve member operatively connected to said distal end of said wire, the perimeter of said sleeve member being smaller than the perimeter of the side holes on the tube, said sleeve member including a first and a second longitudinal section, said first section being operatively connected to and enclosing said distal end of said wire, said second section extending beyond said distal end of said wire to frictionally contact the end wall at the distal end of the bore when said stylet hub is retained in the proximal end of the tube, wherein said sleeve member has a generally uniform external diameter and has a hollow distal end with an internal diameter between 0.6 mm and 0.9 mm.

7. The stylet of claim 6, wherein said second section is longer than said first section.

8. The stylet of claim 6, wherein said sleeve member has a generally uniform external diameter and has a hollow distal end with an internal diameter between 0.6 and 0.9 mm.

* * * * *